(12) United States Patent
Lai

(10) Patent No.: US 10,168,319 B2
(45) Date of Patent: Jan. 1, 2019

(54) METHOD FOR SELECTING AN ANTIGEN-SPECIFIC HYBRIDOMA

(71) Applicant: Green AbioTechnology Co., Ltd, Taichung (TW)

(72) Inventor: Chih-Hsuan Lai, Taichung (TW)

(73) Assignee: GREEN ABIOTECHNOLOGY CO., LTD, Taichung (TW)

(*) Notice: Subject to any disclaimer, the term of this patent is extended or adjusted under 35 U.S.C. 154(b) by 343 days.

(21) Appl. No.: 15/060,990

(22) Filed: Mar. 4, 2016

(65) Prior Publication Data

US 2016/0258952 A1    Sep. 8, 2016

(30) Foreign Application Priority Data

Mar. 6, 2015   (TW) ............................. 104107281 A

(51) Int. Cl.
*G01N 33/50*  (2006.01)
*C07K 16/00*  (2006.01)

(52) U.S. Cl.
CPC ......... *G01N 33/5044* (2013.01); *C07K 16/00* (2013.01); *G01N 2333/70596* (2013.01)

(58) Field of Classification Search
None
See application file for complete search history.

(56) References Cited

U.S. PATENT DOCUMENTS 9,581,602 B2 * 2/2017 Mann ..................... C12M 41/00
9,588,117 B2 * 3/2017 Chapman ........... G01N 33/6854

FOREIGN PATENT DOCUMENTS

JP          2009268399 A      11/2009

* cited by examiner

*Primary Examiner* — Changhwa J Cheu
(74) *Attorney, Agent, or Firm* — Ming Chow; Sinorica, LLC

(57) ABSTRACT

This present invention relates to a method for selecting an antigen-specific hybridomas comprising catching a monoclonal antibody secreted from a hybridoma by using a plasma cell's cell-surface expression molecular on the surface of the hybridoma, providing an antigen with a label to react with the hybridoma, and selecting the hybridoma expressing the label to obtain an antigen-specific hybridoma. In other words, the hybridoma can express the label because of the monoclonal antibody combining with the antigen. Accordingly, the method of this present invention can quickly select the antigen-specific hybridoma.

7 Claims, 5 Drawing Sheets

METHOD FOR SELECTING AN ANTIGEN-SPECIFIC HYBRIDOMA

The current application claims a foreign priority to application number 104107281 filed on Mar. 6, 2015 in Taiwan.

FIELD OF THE INVENTION

This invention relates to preparation of monoclonal antibody, specially relates to a method for selecting an antigen-specific hybridoma.

DESCRIPT OF PRIOR ART

The literature published in 1975 had disclosed the application of hybridomas, hybrid cell lines, in preparation of monoclonal antibody. The prior technology for producing monoclonal antibody was achieved by immunizing the animals through multiple injections with the specific antigens. After immunization, the hybrid cell was generated by fusing a splenocyte of the immunized animal with a myeloma cell within the fusion medium containing polyethylene glycol (PEG). The objective hybrid cell was successfully selected upon the characteristics of myeloma cell and splenocyte including ex vivo viability and DNA synthesis with the selection medium such as HAT medium (hypoxanthine-aminopterin-thymidine medium). Then, the selected hybrid cell was further monoclonalized to produce monoclonal antibody. Finally, the specificity of the monoclonal antibody was determined by ELISA (Enzyme-Linked Immunosorbent Assay).

Generally, it took at least one month for generation of antibody-producing cells by immunization of the animal. Then, it took about 1 day to generate hybridomas by cell fusion reaction and several weeks to identify the hybridomas using HAT medium. Finally, it took one month for the monoclonalization of hybridomas and the determination of antibody specificity.

As is described previously, the monoclonal antibodies can used for diagnosis and therapy, so it is estimated to have a market value of multi-billion dollars. Accordingly, many companies have devoted great effort in shortening the time period of preparation schedule to develop efficient monoclonal antibodies. So far, some technological breakthroughs had been developed in antigen design and immunization to shorten the time cost in immunization. However, there are a few large scale companies using high-throughput screening method by robots to shorten the time period in identifying the antigen-specific hybridomas. The high-throughput screening method by robots cost a lot of money for development, so it will increase the price of the products and can't be widely adopted by all antibody development companies with different capital scales.

Therefore, development of the screening method to rapidly identify an antigen-specific hybridoma is the critical issue in biomedicine industry.

DETAIL DESCRIPTION OF THE INVENTION

The major object of the present invention is to provide a method for selecting an antigen-specific hybridoma comprising catching a monoclonal antibody secreted from a hybridoma by using a plasma cell's cell-surface expression molecular on the surface of the hybridoma, providing an antigen with a label to react with the hybridoma, and selecting the hybridoma expressing the label to obtain an antigen-specific hybridoma. In other words, the hybridoma can express the label because of the monoclonal antibody combining with the antigen. Accordingly, it can quickly select the antigen-specific hybridoma.

Another object of the present invention is to provide the method for selecting the antigen-specific hybridoma which can largely shorten the time cost and rise the efficiency for developing monoclonal antibodies.

Still another object of the present invention is to provide the method for selecting the antigen-specific hybridoma which is quite simple to operate, so it can save the huge cost on buying the equipments. Therefore, the method of this present invention is suitable for all antibody development companies with various capital scales.

In order to achieve these foresaid purposes, the present invention discloses a method for selecting an antigen-specific hybridoma comprising the following steps:

(a) providing a hybridoma and a cell surface marker of plasma cell, wherein the cell surface marker of plasma cell is on the surface of the hybridoma;

(b) combining a target antibody secreted from the hybridoma with the hybridoma by the cell surface marker of plasma cell;

(c) providing an antigen with a label to react with the hybridoma; and (d) selecting an antigen-specific hybridoma which can express the label.

Preferably, there are at least two antibodies between the target antibody and the cell surface marker of the plasma cell, and the two antibodies are linked to each other by a connecting molecule.

Furthermore, the two antibodies are a first antibody and a second antibody, respectively, wherein the first antibody includes a first conjugating molecular binding to the connecting molecule and a first antigen-binding site binding to the cell surface marker of plasma cell, and the second antibody includes a second conjugating molecular binding to the connecting molecule and a second antigen-binding site binding to the target antibody.

Preferably, the first conjugating molecule is biotin.

Preferably, the second conjugating molecule is biotin.

Preferably, the second antibody and the target antibody are derived from different animals.

Preferably, the connecting molecule non-covalently binds to the first or the second antibody. For example, the connecting molecule could be avidin, streptavidin or signal enzyme.

Preferably, the label can be any substance for detection or identification which is known to those skilled in the art. For example, the label is a fluorescent agent, a magnetic agent.

Preferably, the cell surface marker of plasma cell is CD (cluster designation) marker. For example, the cell surface marker of plasma cell is CD138.

Preferably, the hybridoma of the step (a) is obtained by fusing the plasma cell and a myeloma cell.

DETAILED DESCRIPTION OF THE INVENTION

Figure 1:
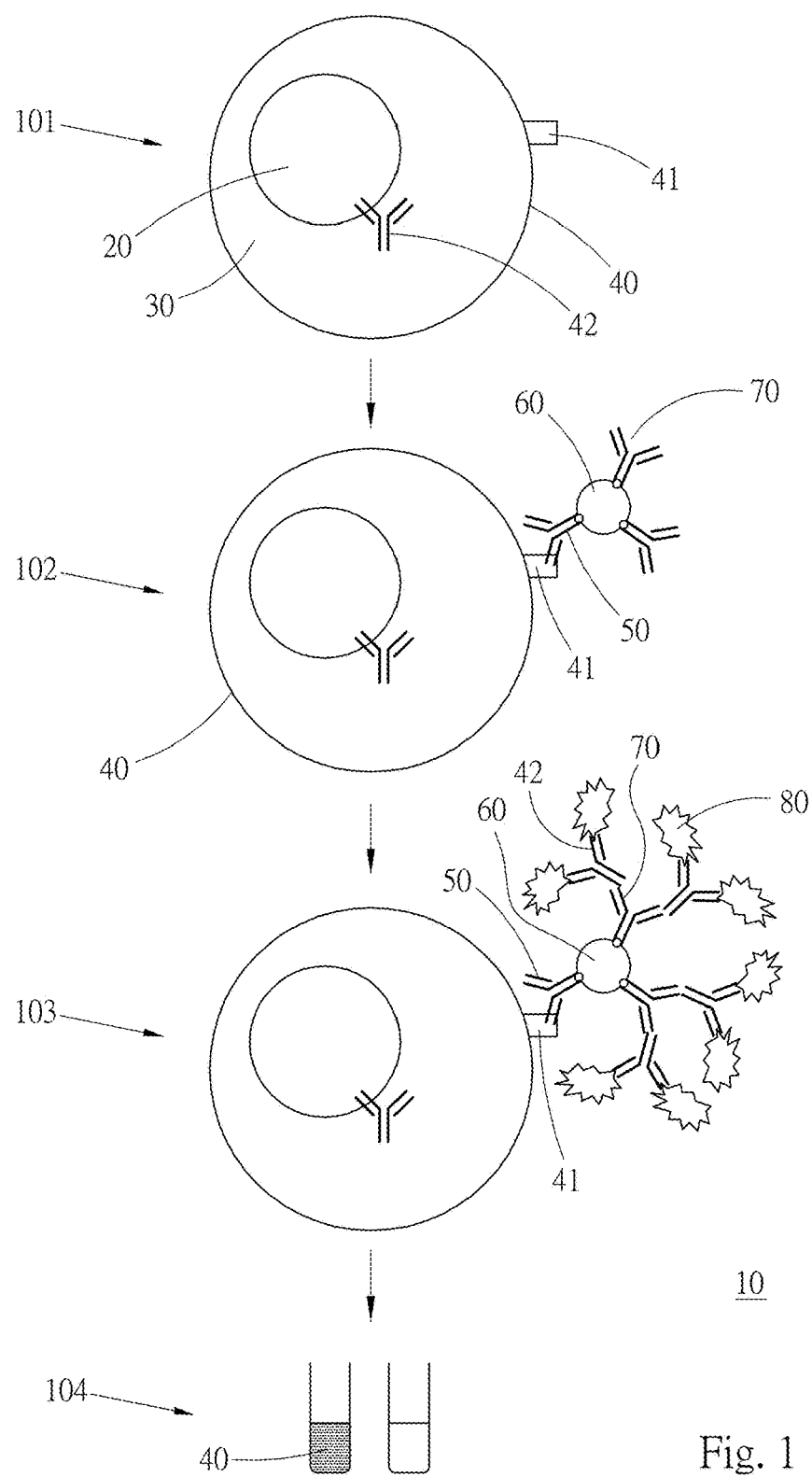
FIG. 1 shows the flow chart of the embodiment of the present invention.

The present invention discloses a method for selecting an antigen-specific hybridoma comprising catching a target antibody secreted from a hybridoma by a cell surface marker of plasma cell located on the surface of the hybridoma, providing an antigen with a label to react with the hybridoma, and then selecting an antigen-specific hybridoma which can express the label. The method of the present invention is able to replace the traditional method using ELISA that determines the specificity of the produced antibody against specific antigen. This method largely shortens the time cost in development of the monoclonal antibodies to response to the marketing requirement. Moreover, the method of the present invention saves the cost in research & development due to the simple and cheap procedure.

The technical term or the scientific term that will be used in the specification has the same meaning as a person skilled in the art commonly understood unless defined differently.

The term "hybridoma", "hybrid cell line" or "hybrid cell" refers to a cell or a cell line that is produced by fusing at least two different cells to one cell. In the present invention, the two different cells are an antigen-immunized splenocyte and a myeloma cell, respectively.

The term "cell fusion method" or "fusion" or "fusing" refers to a method in which two or more cells are combined to form a single hybrid cell which contains all or part of at least the nucleic acid content of each individual cell. Fusion may be accomplished by any method of combining cells under fuseogenic conditions well known in the art. For example, PEG is the most widely used chemical reagent to trigger cell fusion during development of monoclonal antibodies. The cell fusion can be also achieved by the physical method using electric pulse. In addition, the biological method for cell fusion is induced by the inactivated virus.

The term "antigen-immunization" or "antigen-immunized" refers to the first step in generation of the monoclonal antibody. In general, immunizing the animal by injecting a specific antigen to induce the maturation and expansion of B cells is able to stimulate destined antibody production from splenocyte, B cell or plasma cell derived from splenocyte. In addition, immunization is also achieved by treatment of designed antigen on cultured cells to induce antibody production.

The term "tumor cell" is also known as "cancer cell" that bears immortality in cultured medium. Recently, the myeloma cell is the most widely used cancer cell line for preparation of monoclonal antibody. For example, the myeloma cell lines including NS-1 cell, SP2/0 cell, and P3X63Ag8.U1 cells are cancer cell lines derived from BALB/c mice. In addition, the myeloma cell lines including RPMI8226 cell, MC/CAR cell, IM-9 cell, UC 729-6 cell, and LTR228 cell are human cancer cell lines.

The term "fluorescent agent" refers to a fluorescent substance such as fluorescent dye. In biomedicine field, the fluorescent agent is used as a label for detection, measurement, analysis and diagnosis.

The term "magnetic agent" refers to a label such as magnetic bead, which is covalently conjugated with an antibody, used in the magnetic cell sorting system. For example, the cell labeled with a magnetic agent is stalled in the separation column with the magnetic field. While the magnetic field is removed, the cell labeled with magnetic agent is collected from the column to isolate and select the identified cell.

In the following, there are several embodiments with figures for further describing and illustrating the present invention. According to FIG. 1, the embodiment of the present invention discloses a method for selecting an antigen-specific hybridoma (10), which comprises the following steps:

Step 101: Preparation of a hybridoma (40) by fusing an antigen-immunized plasma cell (20) with a myeloma cell (30) according the method of cell fusion, wherein CD138 (41), a cell surface antigen of the plasma cell, was on the surface of the hybridoma.

Step 102: Providing biotin-conjugated anti-CD138 monoclonal antibody (50), avidin (60), and biotin-conjugated anti-mouse Ig monoclonal antibody (70) were sequentially added a culture medium including the hybridoma (40) to be incubated with the hybridoma (40).

Step 103: Providing a fluorescent dye-labeled antigen (80) was added into the culture medium of Step 102, wherein the antigen (80) is the same as the antigen used for inducing immunization of the plasma cell (20) in Step 101.

Step 104: Selecting a hybridoma 40 can express the fluorescence by cell sorting using flow cytometry.

According to the above-mentioned methods, the cell surface marker of plasma cell such as CD138 is utilized to identify the antigen-specific hybridoma through addition of different suitable antibodies and connecting compound. CD138 (41) bound to the antigen binding site of biotin-conjugated anti-CD138 monoclonal antibody (50), and avidin (60) was used to bound to the biotin-conjugated anti-CD138 monoclonal antibody (50) and biotin-conjugated anti-mouse Ig monoclonal antibody (70). Accordingly, the two monoclonal antibodies (50) (70) and avidin (60) formed the connecting chain complex. One end of the connecting chain complex was anchored on the hybridoma by binding with CD138 (41). On another end of the connecting chain complex, the antigen binding site of biotin-conjugated anti-mouse Ig monoclonal antibody (70) is to catch the target antibody (42) secreted from the hybridoma (40).

Because of the specific interaction between the target antibody (42) and the fluorescent dye-labeled antigen (80), while the another end of connecting chain complex binds with the fluorescent dye-labeled antigen (80), the hybridoma (40) can bear the fluorescence by the interaction of the fluorescent dye-labeled antigen (80) and the target antibody (42). Therefore, the hybridoma, which secretes the antigen-specific monoclonal antibody, could be easily identified according to the specific interaction between the target antibody and the fluorescent dye-labeled antigen.

Moreover, the label is not limited to fluorescent agent. The label is any labeled material known to the skilled person in the art, such as magnetic bead.

Furthermore, the main characteristic of the present invention is to combine the target antibody with the hybridoma by a cell surface marker on the hybridoma, such as antigen. As will be understood by a person of skill in the art, the cell surface marker can be modified or replaced. For example, avidin could be replaced by streptavidin or signal enzyme.

The following example with figures are to further demonstrate the present invention.

Example: Cell Fusion

The NS-1 cells transfected with GFP gene were cultured before the cell fusion. On the day before cell fusion, passage of NS-1 cells was performed and was followed by cell culture until the growing cells occupy 50%~60% capacity of culture dish. The cultured cells were collected for centrifugation at 1000 rpm. Then, the supernatant was discarded for re-suspending the cell palate and cell counting.

Prefusion boosting was performed on the immunized mice on 3 days before cell fusion. On the day of cell fusion, spleen was collected from the mouse that was anesthetized by isoflurane. The collected spleen in 200-mesh steel cell strainer, that was placed in 6-cm dish containing 5 ml serum free DMEM, was homogenized to release the splenocytes. The 5 ml splenocyte-containing suspension was then filtered the 70-um cell strainer put on 5 ml centrifuge tube. The 70-um cell strainer was further washed by 10 ml serum free DMEM. 15 ml collected medium was collected for centrifugation at 1000 rpm for 5 minutes to spin down the splenocytes. After discarding the supernatant, 5 ml RBC (Red Blood Cells) lysis buffer was added and was incubated for 5 minutes to lyse the red blood cells. After the incubation, 35 ml serum free DMEM was added to dilute RBC lysis buffer and was centrifuged at 1000 rpm for 5 minutes. After discarding the supernatant, 20 ml serum free DMEM was added to re-suspend the cell plate for cell counting.

NS-1 cell and splenocytes were mixed well in a ratio about 1:1 to 1:5, first. Then, 1~2 ml cell fusion buffer (serum free DMEM with 50% PEG-4000) was added. In the next step, 1~2 ml serum free DMEM was added to be mixed well with cell fusion buffer. Finally, 7 ml serum free DMEM was added and is followed by centrifugation at 1000 rpm for 5 minutes. After discarding the supernatant, the cell plate was re-suspended by 10 ml serum free DMEM and is cultured in cell incubator.

Calculating the number of the hybrid cells was prepared from cell fusion reaction. In addition, some of the hybrid cells were aliquoted as the control group. The others were placed in the centrifuge tube for centrifugation at 1000 rpm for 5 minutes to spin down the hybrid cells. After discarding the supernatant, 1 ml DMEM-20 (20% FBS, 1 mM Sodium pyruvate, 10 mM HEPES, 10 ug/ml gentamicin) was added to re-suspended the cell palate and was further centrifuged at 1000 rpm for 5 minutes. After discarding supernatant, 1 ml staining buffer (PBS, 3% FBS, 0.22 um filtered) was added to re-suspend the cell palate for cell counting. Finally, the hybrid cells-containing suspension was adjusted to the concentration about $5 \times 10^5 \sim 1 \times 10^6$ cells/ml.

The suspension was aliquoted into the 6-wells plate with the indicated cell number indicated in the below table:

| NS1-splenocyte, $5 \times 10^5 \sim 1 \times 10^6$ cells/ml, 1 ml | NS1-splenocyte, $5 \times 10^5 \sim 1 \times 10^6$ cells/ml, 1 ml | NS1-splenocyte, $5 \times 10^5 \sim 1 \times 10^6$ cells/ml, 1 ml |
|---|---|---|
| NS1-splenocyte, $5 \times 10^5 \sim 1 \times 10^6$ cells/ml, 1 ml | NS1-splenocyte, $5 \times 10^5 \sim 1 \times 10^6$ cells/ml, 1 ml | NS1-splenocyte, $5 \times 10^5 \sim 1 \times 10^6$ cells/ml, 1 ml |

10 ul PE-antigen was loaded into each wells and is mixed well for interacting the targeted antibody. In the following, 1 ml DMEM-20 was loaded into each well of the 6 wells plate that was indicated as below table:

| NS1-splenocyte, $5 \times 10^5 \sim 1 \times 10^6$ cells/ml, 2 ml | NS1-splenocyte, $5 \times 10^5 \sim 1 \times 10^6$ cells/ml, 2 ml | NS1-splenocyte, $5 \times 10^5 \sim 1 \times 10^6$ cells/ml, 2 ml |
|---|---|---|
| NS1-splenocyte, $5 \times 10^5 \sim 1 \times 10^6$ cells/ml, 2 ml | NS1-splenocyte, $5 \times 10^5 \sim 1 \times 10^6$ cells/ml, 2 ml | NS1-splenocyte, $5 \times 10^5 \sim 1 \times 10^6$ cells/ml, 2 ml |

The 6 wells plate was incubated at 37° C. for 2 hours and was followed by addition with 3 ml staining buffer to dilute the interaction. The suspension was collected into centrifugation tube for centrifugation at 1000 rpm for 5 minutes. After discarding the supernatant, 1 ml staining buffer was added to re-suspend the cell palate and was filtered through 70-um cell strainer. After cell counting, the cells were screened and sorted by using fluorescence activation cell sorter (FACS).

Figure 2:
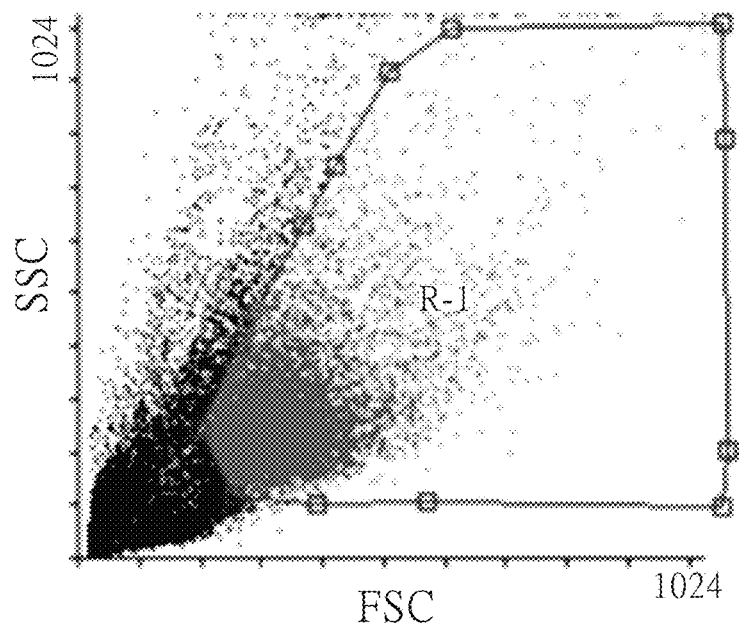
FIG. 2 shows the dot plots of FSC versus SSC with R-1 region by Flow cytometry.
Figure 3:
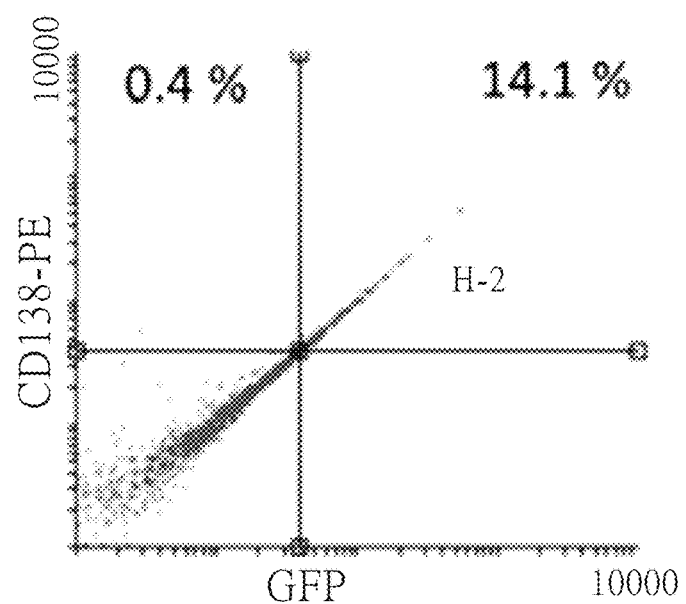
FIG. 3 shows the result for counting the ratio of the fusion cells in R-1 region.
Figure 4:
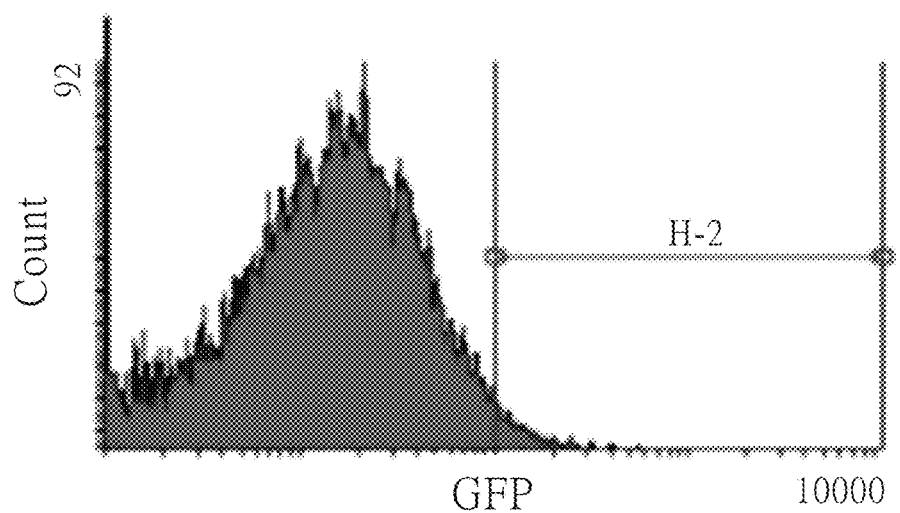
FIG. 4 shows the result for analyzing the ratio of the cells with enhanced-GFP fluorescence intensity.
Figure 5:
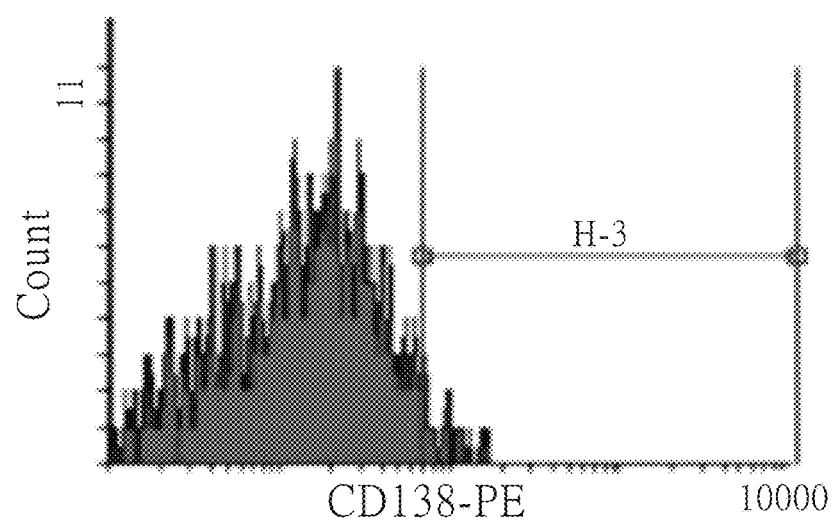
FIG. 5 shows the result for analyzing the ratio of the cells having the CD-138 PE signal.
Figure 6:
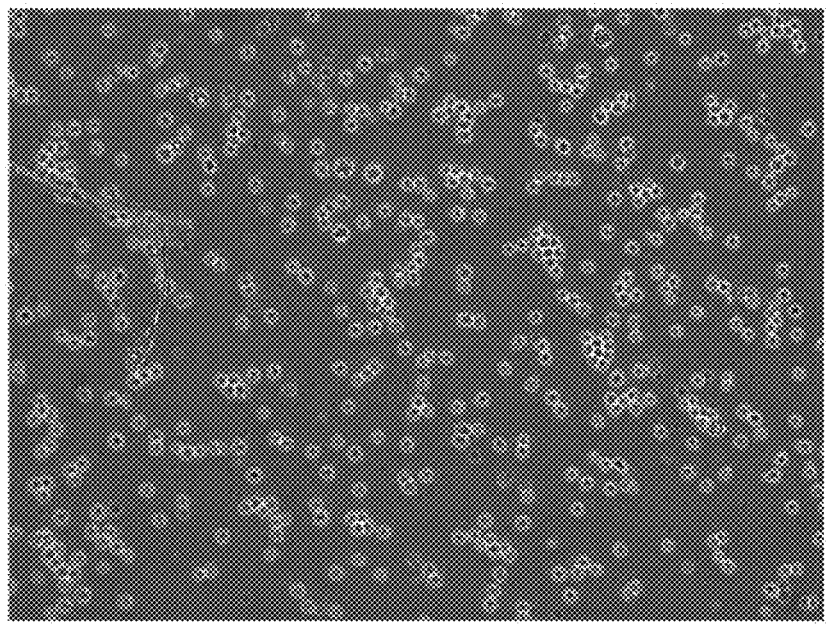
FIG. 6 shows the result of observing the cultured cells by microscopy.
Figure 7:
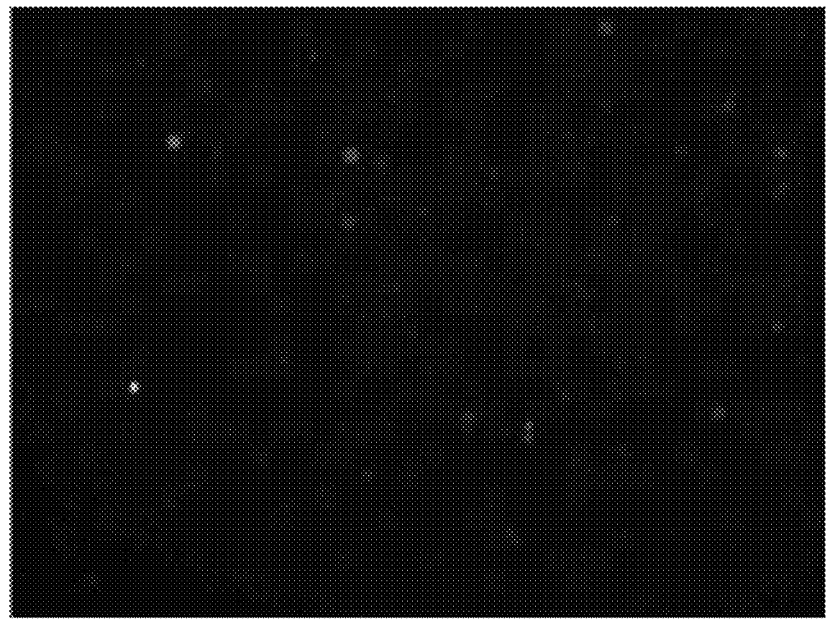
FIG. 7 shows the result of observing the cultured cells by fluorescent microscopy.
Figure 8:
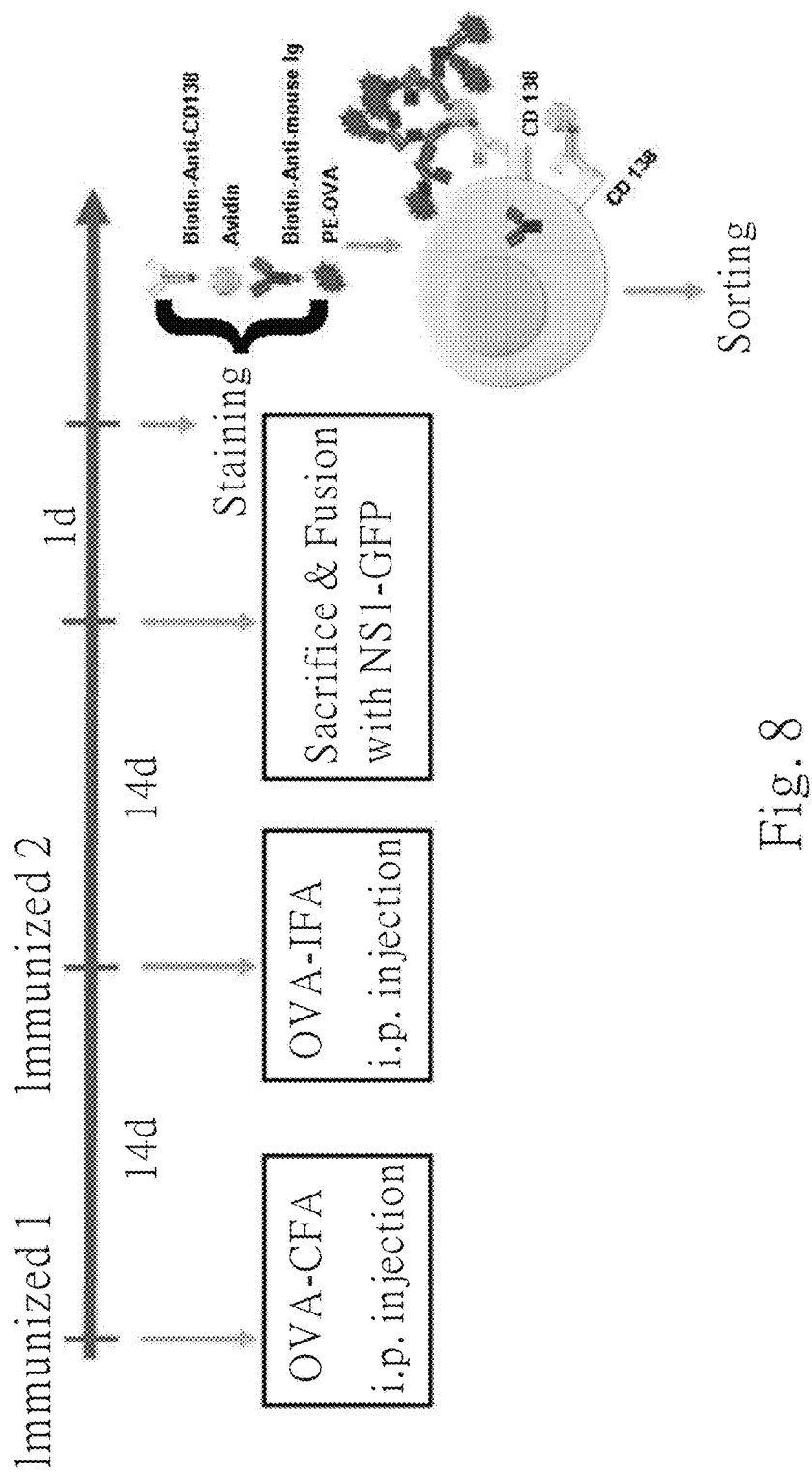
FIG. 8 shows the time schedule of the present invention.

Please see the FIGS. 2 to 7, it shown that the cell area is R-1 in the FIG. 2. The hybridomas of the cell area are 14.1% (as shown in H-2 of FIG. 3). There are 2.72% cells express the enhanced fluorescence intensity of GFP (as shown in H-2 of FIG. 4) and 6.12% cells express the signal of CD 138 interacting with PE-antigen PE (as shown in H-3 of FIG. 5). Accordingly, the hybridoma cell generated by fusing a green-fluorescent NS-1 cell with a splenocyte from normal mouse is identified by the cell surface marker, CD138, which interact with PE-antigen. Moreover, as shown in FIG. 8, it suggests that this present method is able to efficiently shorten the time cost for identifying the hybridoma that secretes monoclonal antibody against the specific antigen.

The above-mentioned detailed description and specific examples are only for illustrating of this present invention. Any easy change or modification based on examples in the description by the person skilled in the art of this present invention will be included within the scope of following claims.

What is claimed is:

1. A method for selecting an antigen-specific hybridoma includes the following steps:
    (a) providing a hybridoma by fusing an antigen-immunized plasma cell with a myeloma cell, and a cell surface marker of plasma cell, wherein the cell surface marker of plasma cell is on the surface of the hybridoma;
    (b) combining a target antibody secreted from the hybridoma with the hybridoma by the cell surface marker of plasma cell, and providing a first antibody and a second antibody that have been added to the hybridoma, wherein the first antibody comprises a first conjugating molecule that binds to a connecting molecule, and a first antigen-binding site binds to the cell surface marker of the plasma cell, and wherein the second antibody comprises a second conjugating molecular that binds to the connecting molecule of the first antibody, and a second antigen-binding site binds to the target antibody;
    (c) providing an antigen with a label to react with the hybridoma, wherein the antigen with the label is the same as the antigen used for inducing immunization of the plasma cell; and
    (d) selecting an antigen-specific hybridoma which can express the label.

2. The method for selecting an antigen-specific hybridoma to claim 1, wherein the first conjugating molecule is biotin.

3. The method for selecting an antigen-specific hybridoma to claim 1, wherein the second conjugating molecule is biotin.

4. The method for selecting an antigen-specific hybridoma to claim 1, wherein the connecting molecule is selecting from the group consisting of avidin and streptavidin.

5. The method for selecting an antigen-specific hybridoma to claim 1, wherein the second antibody and the target antibody are derived from different animals.

6. The method for selecting an antigen-specific hybridoma to claim 1,
   wherein the label is selecting from the group consisting of fluorescent agent and magnetic agent.

7. The method for selecting an antigen-specific hybridoma to claim 1,
   wherein the cell surface marker of plasma cell is CD (cluster designation) marker.

\* \* \* \* \*